United States Patent [19]
Meehan

[11] Patent Number: 5,879,622
[45] Date of Patent: Mar. 9, 1999

[54] METHOD AND COMPOSITION FOR NEUTRALIZING OFFENSIVE ODORS

[76] Inventor: Frank Meehan, 203 Cathedral Ave., Hempstead, N.Y. 11550

[21] Appl. No.: 13,653

[22] Filed: Feb. 3, 1993

Related U.S. Application Data

[63] Continuation of Ser. No. 318,909, Mar. 3, 1989, abandoned.

[51] Int. Cl.⁶ ........................................ A61L 9/00
[52] U.S. Cl. .................. 422/5; 422/1; 422/5; 422/122; 424/76.5; 424/76.6; 424/76.7; 424/76.3
[58] Field of Search ................... 422/1, 5, 122; 424/76.5, 76.6, 76.7, 76.3

[56] References Cited

U.S. PATENT DOCUMENTS

| | | | |
|---|---|---|---|
| 3,675,675 | 7/1972 | Miller et al. | 119/1 |
| 4,218,432 | 8/1980 | Watanabe et al. | 424/78 X |
| 4,567,613 | 2/1986 | Meehan | 4/222 |
| 4,633,533 | 1/1987 | Meehan | 4/222 |
| 4,861,583 | 8/1989 | Sramek | 424/70 |

OTHER PUBLICATIONS

*Webster' Ninth New Collegiate Dictionary*, Merriam–Webster Inc. 1986, pp. 742.

The Condensed Chemical Dictionary, Van Nostrand Reinhold Co., New York, (1971) 8th Ed., pp. 218, 514,549,550, 667.

*Primary Examiner*—William H. Beisner
*Attorney, Agent, or Firm*—Ladas & Parry

[57] ABSTRACT

Scatalogical and other offensive odors are neutralized by prior deposit into a receptacle of drops of an alcoholic solution of menthol, peppermint oil and a pleasant smelling oil such as lemon oil. The menthol is present in an amount of 10% by weight, the lemon oil is present in an amount of 7.5% by weight, and the peppermint oil is present in an amount of 1% by weight.

9 Claims, 2 Drawing Sheets

METHOD AND COMPOSITION FOR NEUTRALIZING OFFENSIVE ODORS

This is a continuation of application Ser. No. 07/318,909 filed on Mar. 3, 1989, now abandoned.

FIELD OF THE INVENTION

The invention relates to a method and composition for neutralizing offensive odors particularly those produced by fecal matter.

The invention also relates the combination of a dispenser container and liquid odor neutralizing composition.

The invention has particular applicability for use in toilets and, particularly, where disposal may not be immediate, such as bedpans and portable toilets and on small boats, buses and the like.

The invention also has special applicability to use in small quarters with poor ventilation.

BACKGROUND

In my prior U.S. Pat. Nos. 4,567,613 and 4,633,533, I have disclosed various articles, methods and means for dispersing liquid deodorant for neutralizing offensive odors.

SUMMARY OF THE INVENTION

The invention is based on improvements relating to the composition of the deodorant and its mode of storage and dispensing.

By virtue of the improvements according to this invention, the objectives set forth in my earlier patents are substantially enhanced. These include the following:

An article which is capable of use both in the presence or absence of water.

An inexpensive package and associated method which will enable use in toilet facilities with or without water.

A throwaway article which is relatively inexpensive and which is capable of being carried for activation at the time of use.

A throwaway article which will allow itself to be activated without contaminating either the user or his or her surroundings.

A throwaway article of the above character which employs a minimal quantity of active substance and which is readily disposable.

A throwaway article which is openable by peeling and which is introduced into the toilet facility prior to use and is thereafter flushed away, leaving no scent behind.

According to the invention, a novel liquid deodorant composition is provided which is adapted for use in articles and containers disclosed in my earlier patents to achieve neutralization of offensive odors in unique fashion.

The novel liquid deodorant composition essentially comprises an alcoholic solution of menthol.

It has been found that the composition is of maximum effectivity when the menthol is present in an amount of about 10% by weight. There is a diminution of effectivity when the amount of the menthol is increased or decreased, and outside the range of 5–15%, the composition is not effective.

A preferred alcohol for dissolving the menthol is anhydrous ethanol as this does not have any deleterious effect on the deodorizing properties of the menthol, does not disseminate any substantial odor into the environment of use and allows the menthol to perform its deodorizing function.

The alcoholic menthol solution adds little if any odor to the environment and is capable of absorbing obnoxious odors from fecal matter. Accordingly, the alcoholic menthol is administered into the receptacle into which fecal matter is to be deposited before such deposit in order to neutralize the offensive odor.

In order to impart a slight pleasant scent into the odor neutralized environment, the invention contemplates the addition to the alcoholic menthol solution of pleasant smelling oils which are compatible with the menthol and have no adverse influence on its efficiency as a neutralizer of scatalogical odors.

In further accordance with the invention, the pleasant smelling oils which will satisfy these conditions are a carefully balanced mixture of peppermint oil and lemon oil. It has been determined that the peppermint oil is effective with the menthol because of their molecular similarity whereas the lemon oil has a balancing property to the more intense odor of the peppermint oil. These oils are effective in the alcoholic menthol solution when they are incorporated in the amount of 0.2 to 4.0% by weight of the peppermint oil and 2.0 to 15% by weight of the lemon oil.

The deodorant composition of the invention can be placed In articles as disclosed in U.S. Pat. No. 4,567,613 or in containers disclosed in U.S. Pat. No. 4,633,533.

The deodorant composition is volatile and evaporates rapidly in droplet form. When added to water, it is highly dispersed on the surface of the water.

Relatively small amounts of the product are effective to absorb offensive odors and only several drops are needed to neutralize the odor of a human bowel movement. The presence of the peppermint oil and lemon oil confers a mild, pleasant scent to the otherwise neutralized environment.

An essential aspect of the invention is that the deodorant composition and its associated method of use does not contemplate after-usage in the manner of conventional cover-up sprays which leave a residual odor which, in many cases, itself is offensive but, rather, it is deposited into the toilet facility after which it is removed along with the offensive material. The odor neutralizing liquid directly counteracts the offensive odor in a generally substantially confined environment.

It has been discovered that the evaporative properties of the composition of the invention are counteracted when the composition is placed in a flexible container having a discharge opening or aperture of calibrated size. Namely, the size of the opening is such that it prevents evaporation of the composition while allowing dropwise discharge therefrom when the container is inverted and squeezed. Hence, the invention also relates to the combination of the liquid composition in the flexible container whereby the container will have long shelf life without evaporation of the contents even should the discharge aperture be left exposed.

In order to increase the viscosity of the liquid solution so that it can be placed into a sealed packet, such as in an article of the type in U.S. Pat. No. 4,567,613, the solution can be emulsified. Thereby, the emulsified liquid solution will not flow freely when the article is opened for use.

According to the invention, an emulsifier has been found which is compatible with the odor neutralizing liquid insofar that it does not have any deleterious effect thereon and does not confer any odor of its own. The emulsifier comprises a minimum amount of a carbomer of the order of 1% by volume of the odor neutralizing liquid. The emulsifier has substantially no effect on the odor neutralizing properties of the solution or the imparting of the pleasant scent of the lemon oil and peppermint oil to the ambient atmosphere.

Surprisingly, and in further accordance with the invention, it has been found that the carbomer emulsifier also renders the odor neutralizing solution more volatile.

DETAILED DESCRIPTION OF THE PREFERRED EMBODIMENTS

Figure 1:
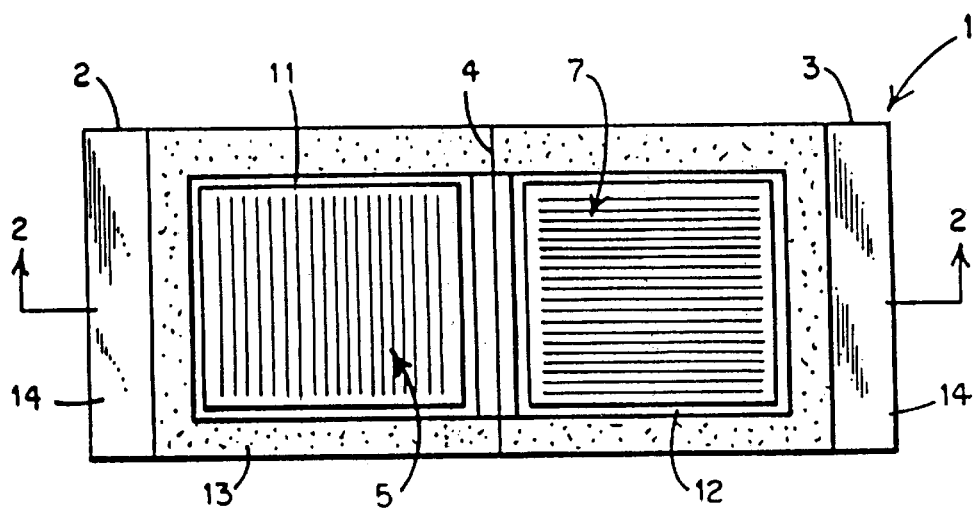
FIG. 1 is a plan view of an article corresponding to that in U.S. Pat. No. 4,567,613 into which the odor-neutralizing solution of the invention can be deposited.
Figure 2:
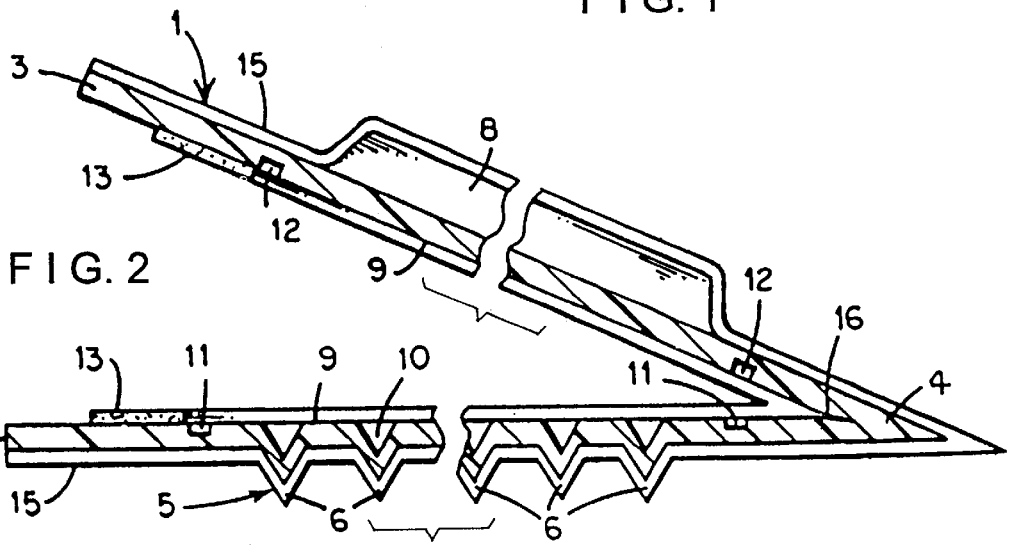
FIG. 2 is a sectional view taken along line II—II with the throwaway article partially folded towards the closed state.

In the drawing is illustrated a throwaway or disposable article 1 for neutralizing offensive odors. The article 1 comprises a sheet of material having portions 2 and 3 foldably joined at a fold line or hinge 4. The hinge 4 is formed by removing material at the join line of portions 2 and 3 so that the portions can be folded into confronting relation as shown in FIG. 2 where the article is in the partially folded state.

Portion 2 includes a grid region 5 composed of a series of parallel crenalations 6 adapted for adsorbing liquid, as will be explained more fully later. The portion 3 also includes a grid region 7 whose crenalations 8 extend in a direction perpendicular to crenalations 6.

When the portions 2 and 3 are folded into confronting relation, flat surfaces 9 of the portions in the grid regions 5 and 7 will come into confronting relation in order to substantially isolate the hollows 10 of the crenalations 6 in which the liquid is contained. In this way, the adsorbed liquid will be divided up into multitudes of miniscule droplets which will be readily adsorbed in the hollows.

The crenalations in the grid regions 5 and 7 expand the surface area of the portions 2 and 3 of the sheet to break up the liquid droplet so that it can be adsorbed over the surface area as a non-flowable film in the confined region. As a consequence, when the article is opened, the liquid will not splatter on the user.

Under certain circumstances, it may be possible to utilize only one grid on one portion and instead of the illustrated construction of the grid formed by the crenalations, it may be possible to provide a surface treatment of the material such as by roughening the surface thereof to achieve the adsorbtion of the liquid.

Encircling the grid region 5 is a continuous groove 11, while surrounding the grid region 7 is a continuous groove 12. The grooves 11 and 12 isolate the grid regions 5 and 7 and the liquid therein from the remainder of the article for a purpose which will become evident hereafter.

Surrounding the grid regions in both portions 2 and 3 is an adhesive border 13. When the sheet is folded around hinge 4, the adhesive border seals itself by contact at both portions. It is noted that the grooves 11 and 12 isolate the adhesive border 13 in order to prevent any contact between the liquid in the grid regions and the adhesive. The grooves 11 and 12 also flank the hinge 4 to prevent any penetration of liquid to the hinge which could lead to splatter upon opening of the article.

When the article is closed and the adhesive border 13 has been brought into contact from both portions, the penetration of liquid to the hinge which could lead to splatter upon opening of the article.

When the article is closed and the adhesive border 13 has been brought into contact from both portions, the article is in readiness for use. A pair of bare tabs 14 are formed at the opposite ends to serve as an engagement means which will allow the user to open the article. The adhesive in the border 13 allows the article to be opened by application of separating pressure to the tabs 14.

The material of the article 1 can be of wide ranging composition provided that it is impermeable to the liquid which is adsorbed in the grid regions. Moreover, not only must it be impermeable to the liquid, it must also be impermeable to the odor thereof. A suitable material for the sheet of the article is polyethylene or PET and it can have a thickness of the order of 0.003 to 0.010 inches. There are numerous adhesives currently available on the market, as will be well known to those skilled in the art and not requiring any elaboration herein. Preferably, however, the material of article 1 is a polyethylene-type film sold by 3M under the trademark SCOTCHPAK 122. This material is heat sealable in region 13 without adhesives and can be peeled open after heat sealing. The material also does not react with the odor neutralizing liquid of the invention and is impermeable to the liquid and to the mild scent thereof.

The liquid which is adsorbed in the grid regions 5 and 7 is intended to serve the function of neutralizing offensive odors, particularly those produced by human fecal matter, and it is intended that the entire article 1 can be opened at the time of use to expose the adsorbed liquid in the grid regions to the ambient atmosphere prior to the use of a toilet facility.

The liquid is an alcoholic solution of menthol and specifically about 10% of menthol by weight dissolved in anhydrous ethanol. In addition to the menthol which is the odor neutralizing component, compatible oils having mild, pleasant odor-producing scents are added to the solution. These are lemon oil and peppermint oil.

A specific example of the odor neutralizing solution is as follows:

| Ingredient | % by weight |
| --- | --- |
| Menthol | 10% |
| Lemon oil | 7.5% |
| Peppermint oil | 1.0% |
| Anhydrous ethanol | 81.5% |

In order to prepare the odor neutralizing solution, the menthol, lemon oil and peppermint oil are added to the anhydrous ethanol with stirring to effect dissolution therein.

The odor neutralizing solution will float on water as a highly dispersed film. The solution is air activated and molecularly interactive in the air to counteract offensive odors and leave a mild pleasant odor from the oils. As a consequence, the deodorant will be extremely effective when the article 1 is opened and dropped into a toilet bowl.

In order to increase the viscosity of the odor neutralizing solution, it can be emulsified before it is applied to the article. In order to achieve emulsification of the solution without impairing the odor neutralizing efficacy of the menthol or the scent of the oils, the odor neutralizing solution is mixed with 1% by volume of a carbomer, such as CARBOPOL 934 and/or 940 sold by B.F. Goodrich mixed with ½% by volume of triamylamine. The emulsifier has no significant effect on the deodorizing properties of the solution. Surprisingly, the emulsified odor neutralizing solution is more volatile than the unemulsified solution.

By way of example, the emulsified solution will evaporate at a rate at least twice as great as that of the unemulsified solution. Nevertheless, the emulsified solution has much greater viscosity than the unemulsified solution. If one droplet of unemulsified solution is placed on a flat surface of one of the portions 2, 3 and the surface faces downward, the droplet will fall by gravity from the sheet despite the adsorbability of the sheet to the liquid. However, under the same conditions, three droplets of emulsified liquid will be retained on the sheet without dropping off.

Because of the composition of the emulsified odor neutralizing solution, the crenelations 6 and 8 in grid regions 5 and 7 can be omitted and the portions 2 and 3 can be made flat to form a pocket in which droplets of the emulsified solution can be retained. When the package is opened, the droplets will not run and contact the hands of the user. For the unemulsified solution, either the crenelations can be present or an absorbable layer can be provided into which the solution can be absorbed.

While the invention has been described with reference to a preferred embodiment in the above example, the amount of the ingredients can be varied within limits to obtain operative results. However, when departing from the amounts in the specific example, the efficacy of the solution is reduced even though it remains operative. The following example represents operative ranges for the individual ingredients.

| Ingredient | % by weight |
| --- | --- |
| Menthol | 5–15 |
| Lemon oil | 2–15 |
| Peppermint oil | 0.2–4 |
| Anhydrous ethanol | 70–92.8 |

The amount of liquid which is added to the article is of the order of 2 to 3 drops. The article 1 is utilized prior to evacuation by opening the article and depositing it into the facility which is to be used. Generally, the odor neutralizing solution acts in a captive atmosphere and is effective by molecular interaction to destroy the malodor. When the toilet is flushed, the article 1 is flushed away and there is no lingering deodorant scent except for the mild odor of the oils. This is in contrast with conventional sprays and slow-release liquids which operate by masking offensive odors. Indeed, these frequently are offensive to the users.

Figure 3:
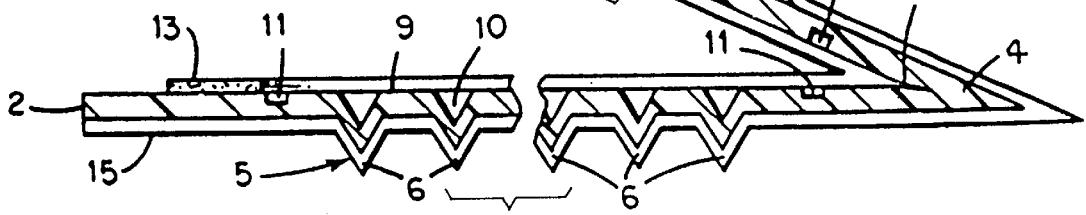
FIG. 3 is a diagrammatic illustration showing the article in unfolded, ready to use, state after it has been deposited on a flat surface.

Since it is also contemplated for the article 1 to be utilized under non-aqueous conditions, such as bedpans, it is important that the article when opened not be capable of being rendered ineffective such as by a smothering action on the liquid in the grid regions. For this purpose, the hinge or fold-line 4 is constructed so that it opposes opening of the portions 2 and 3 into a flat condition. This is achieved when the article is provided with the thickness previously indicated and with the formation of a shallow V-groove 16 for the formation of the hinge wherein the remaining thickness of the material at the groove 16 is a minor portion of the thickness of the material. As a consequence, there will be a natural bias built into the material tending to return it to a partially folded position whereby if the article lands face down, as shown in FIG. 3, there will be a space 17 formed beneath the article to allow circulation of air so that the liquid solution can serve the odor neutralizing function.

The odor neutralizing solution can also be added to a container for dropwise discharge therefrom when the solution is to be used.

Figure 4:
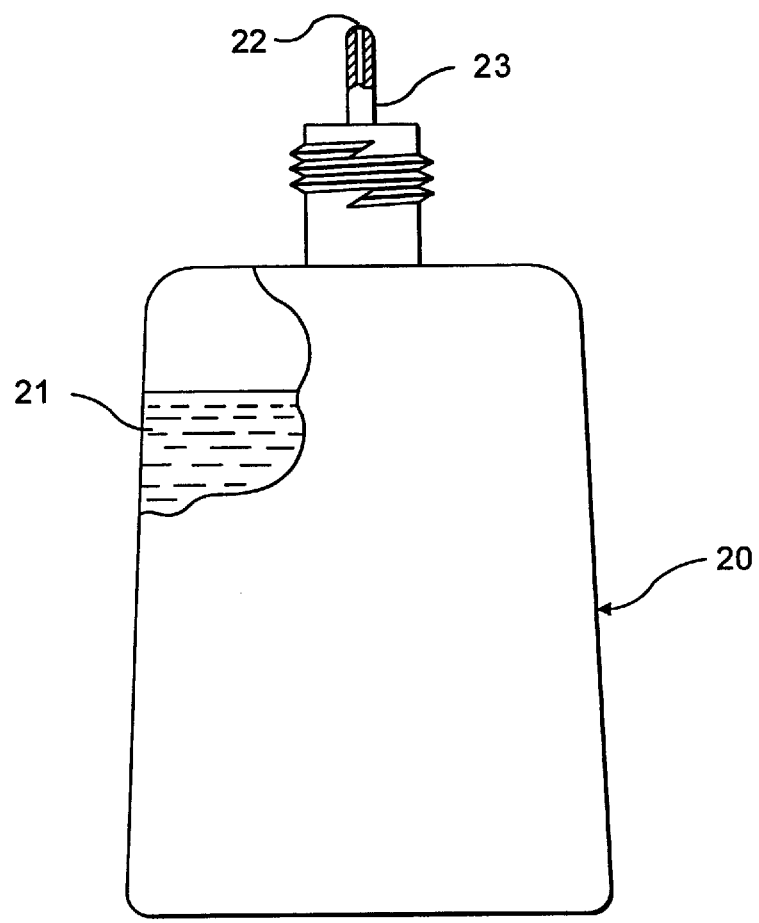
FIG. 4 is an elevation view, partly broken away and in section, of a container with the cap removed which is adaptable for use with the odor-neutralizing solution of the invention.

In FIG. 4 is seen a flexible container 20 in which the solution 21 has been added. The container can be made of polyethylene which is compatible with the odor neutralizing solution of the invention so as not to affect its odor neutralizing properties while storing the solution without transmitting its odor through the container.

The container 20 is sufficiently flexible so as to be squeezable so that when the container is inverted and squeezed, the liquid 21 will be discharged dropwise through a calibrated bore 22 in a nozzle 23.

The calibrated bore 22 is so dimensioned that an equilibrium condition will be obtained in the container 20 for the solution 21 so that the solution will not evaporate from the container. This is a surprising discovery since the solution 21 is relatively volatile and rapidly evaporates in the air. The diameter of the bore 22 which will block evaporation of the alcoholic menthol solution while permitting dropwise discharge thereof is between 0.8 and 1.3 mm. While the exact reason for the blockage of evaporation is not completely understood, it is assumed that a pressure equilibrium is established between the evaporated liquid in the free head space in the container and the ambient pressure which prevents further evaporation of the liquid solution in the container. It has been found that with the cap of the container removed and the nozzle exposed to the atmosphere, there is virtually no loss of liquid over a six month period. There is no crystal formation in the calibrated bore as the liquid is immediately dispensed dropwise when the container is inverted and squeezed irrespective of the length of time the cap has been removed. Initially when the cap is removed from the container, the mild odor of the neutralizing solution can be detected, but after several minutes this odor disappears indicating no evaporative loss of liquid.

Although the invention has been disclosed in relation to specific embodiments and compositions thereof, it will become apparent to those skilled in the art that numerous modifications and variations can be made without departing from the scope and spirit of the invention as defined in the attached claims.

What is claimed is:

1. A method of neutralizing scatological odors comprising providing a receptacle into which fecal matter is to be discharged, depositing into said receptacle at least one drop of a solution comprising menthol dissolved in a further alcohol in a concentration of 5–15% by weight, said solution having substantially no odor and being effective to neutralize the odor of the fecal matter by absorption.

2. A method as claimed in claim 1 wherein the alcohol in which the menthol is dissolved is anhydrous ethanol.

3. A method as claimed in claim 1 comprising forming an emulsion of said alcoholic solution, sealing at least one drop of said solution in a sealed openable package, opening said package and dispensing said drop of solution into said receptacle.

4. A method as claimed in claim 3 wherein said emulsion is formed by emulsifying said solution with 1% carbomer.

5. A method as claimed in claim 1 wherein said depositing of said alcoholic solution of menthol into the receptacle is effected by discharging said solution dropwise from a container.

6. A method as claimed in claim 5 wherein the dropwise discharge of solution is effected by squeezing the container in inverted state above said receptacle and discharging the solution through a sized aperture in the receptacle.

7. A method of neutralizing scatological odors comprising providing a receptacle into which fecal matter is to be discharged, depositing into said receptacle at least one drop of a solution containing an alcohol into which are dissolved 5–15% by weight menthol.

0.2–4% by weight peppermint oil, and a further oil having pleasant smelling properties.

8. A method as claimed in claim 7 wherein said pleasant smelling oil further comprises lemon oil.

9. A method as claimed in claim 8 wherein the lemon oil is present in said solution in an amount of 2 to 15% by weight.

* * * * *